United States Patent [19]
Bastos

[11] Patent Number: 5,512,687
[45] Date of Patent: Apr. 30, 1996

US005512687A

[54] COMPOUNDS FOR INHIBITING IMMUNE RESPONSE

[75] Inventor: Cecilia M. Bastos, Westborough, Mass.

[73] Assignee: Procept, Inc., Cambridge, Mass.

[21] Appl. No.: 331,388

[22] Filed: Oct. 28, 1994

[51] Int. Cl.⁶ .............................. A61K 33/24; C07F 1/00
[52] U.S. Cl. .............................. 548/101; 544/225; 546/2
[58] Field of Search .................... 548/103, 101; 544/225, 64; 514/184, 186, 187; 546/4, 2

[56] References Cited

U.S. PATENT DOCUMENTS

| | | | |
|---|---|---|---|
| 4,549,018 | 10/1985 | Siedle | 544/225 |
| 4,843,069 | 6/1989 | Keller et al. | 514/184 |

*Primary Examiner*—Johann Richter
*Assistant Examiner*—Laura R. Cross
*Attorney, Agent, or Firm*—Hamilton, Brook, Smith & Reynolds

[57] ABSTRACT

Novel ruthenium complexes for use as immunosuppressive agents to prevent or significantly reduce graft rejection in organ and bone marrow transplantation are described. The ruthenium complexes can also be used as an immunosuppressant drug for T-lymphocyte mediated autoimmune diseases, such as diabetes, and may be useful in alleviating psoriasis and contact dermatitis.

5 Claims, No Drawings

COMPOUNDS FOR INHIBITING IMMUNE RESPONSE

BACKGROUND OF THE INVENTION

Replacement of defective or severely injured tissues and organs has been a medical objective as long as medicine has been practiced. Grafts from an individual to himself almost invariably succeed, and are especially important in the treatment of burn patients. Likewise, grafts between two genetically identical individuals almost invariably succeed. However, grafts between two genetically dissimilar individuals would not succeed without immunosuppressive drug therapies. The major reason for their failure is a T cell mediated immune response to cell-surface antigens that distinguish donor from host.

Immunosuppressive agents are also indicated in the treatment of autoimmune diseases such as rheumatoid arthritis or type I diabetes mellitus. One particular condition worth mentioning here is psoriasis. This disease is characterized by erythematous patches of skin accompanied by discomfort and itching. Hyperplasia of the epidermis involving proliferation of keratinocytes is also a hallmark feature of psoriasis. An inflammatory component is suggested by: (i) the finding of lymphocytic infiltration of epidermis, and (ii) the fact that immunosuppressive agents such as cyclosporin and corticosteroids have beneficial effect on the disease.

A number of drugs are currently being used or investigated for their immunosuppressive properties. Among these drugs, the most commonly used immunosuppressant is cyclosporin A. However, usage of cyclosporin has numerous side effects such as nephrotoxicity, hepatotoxicity and other central nervous system disorders. Thus, there is presently a need to investigate new immunosuppressive agents that are less toxic but equally as effective as those currently available.

SUMMARY OF THE INVENTION

This invention relates to novel ruthenium complexes that are useful as immunosuppressive agents to prevent or significantly reduce graft rejection in organ and bone marrow transplantation. The ruthenium complexes can also be used as an immunosuppressant drug for T lymphocyte mediated autoimmune diseases, such as diabetes, rheumatoid arthritis, multiple sclerosis, lupus erythematosus and steroid resistant asthma.

In another aspect, other diseases with suspected inflammatory components, such as psoriasis, contact dermatitis and hyperplasia of the epidermis, can be treated with a ruthenium complex of this invention to alleviate symptoms associated with these disease states.

DETAILED DESCRIPTION OF THE INVENTION

This invention is based upon the discovery that ruthenium complexes can inhibit antigen specific T lymphocyte proliferation in vitro. The data suggest that ruthenium complexes have potential use as immunosuppressants to reduce undesirable immune responses in humans. Ruthenium complexes can be used to facilitate organ transplantation, and to treat human autoimmune disorders where the specific activation of T cells is responsible for, or contributes to the pathology and progression of the diseases, such as diabetes, rheumatoid arthritis, multiple sclerosis, lupus erythematosus and steroid resistant asthma.

This invention pertains to novel ruthenium complexes that have immunosuppressive properties of the general formula:

$$[RuM_m B_b T_t]Z_n$$

wherein Ru is ruthenium having an oxidation state of 2, 3 or 4;

wherein M is a monodentate ligand that is a heterocyclic aromatic amine;

wherein m is 0, 1, 2, 3, 4 or 6;

wherein b is 0, 1, 2 or 3;

wherein t is 0, 1 or 2;

wherein B is a bidentate ligand that is a heterocyclic aromatic amine;

wherein T is a tridentate ligand that is a heterocyclic aromatic amine;

wherein Z is a counterion, for example a counterion selected from the group consisting of $F^-$, $Cl^-$, $Br^-$, $I^-$, $NO_3^-$, $NH_4^+$, $NR_4^{1+}$, $PF_6^-$, $SO_4^{-2}$, $R^1ImH^+$, $BPh_4^-$ and $ClO_4^-$;

wherein Im is imidazole wherein n is 0, 1, 2, 3 or 4; and wherein $R^1$ is a linear or branched alkyl of 1–4 carbon atoms or aryl; provided that the ligands cannot be pyridine or pyrazine or derivatives of these.

The coordination sphere of the metal center may contain all six ligands (referred to as monodentate) to be equivalent or a mixture of different ligands. The mixture of ligands can consist of different monodentate ligands; a mixture of bidentate/monodentate in a ratio of 1:4 or 2:2; three bidentate ligands; a mixture of bidentate/tridentate/monodentate in a ratio of 1:1:1; two tridentate ligands; or tridentate/monodentate in a 1:3 ratio.

For the purposes of this application, the terms "monodentate", "bidentate" and "tridentate" will have their generally accepted meaning in the art. That is, a monodentate ligand is defined as a chemical moiety or group which has one potential coordinating atom. More than one potential coordinating atom is termed a multidentate ligand where the number of potential coordinating atoms is indicated by the terms bidentate, tridentate, etc.

The ruthenium metal can have different oxidation states, e.g., Ru(II), Ru(III) or Ru(IV). The complex will also contain a counterion of appropriate charge to render the overall charge of the complex neutral. Suitable counterions for cationic complexes, include but are not limited to, halide ($F^-$, $Cl^-$, $Br^-$ or $I^-$), $SO_4^{-2}$, $PF_6^-$, $BPh_4^-$, $ClO_4^-$ and $NO_3^-$. Examples of suitable counterions for anionic complexes include but are not limited to $NH_4^+$, $NR_4^{1+}$ and $R^1ImH^+$ where $R^1$ is a linear or branched alkyl of 1 to 4 carbons or aryl group and Im is imidazole.

In one embodiment, the ruthenium complex can comprise six monodentate heterocyclic aromatic amine ligands. Examples of suitable heterocyclic aromatic amine ligands include but are not limited to imidazole, triazole, pyrazole, quinoline, pyridazine, pyrimidine, quinoxaline, quinazoline and isoquinazoline. Derivatives of these ligands can also be incorporated into the complex in various combinations with the non-substituted ligands. A derivative is a ligand in which one or more of the hydrogen atoms has been substituted with a moiety, such as C1–C5 alkyl, C2–C4 alkenyl, hydroxy, nitro, amino, carboxyl, ester, di-C1–C4 alkyl amine, phenyl, benzyl, imidazole and combinations of these. Preferred ligands are imidazole derivatives having the general formula:

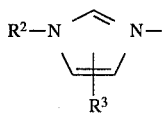

where $R^2$ and $R^3$ are independently selected from the group consisting of aryl, heteroaryl, linear and branched alkyl (e.g., 1 to 8 carbons), —C(O)H, —COOR$^1$, —CONR$^1$, —COOH, H, Cl, Br, I NO$_2$ and methyl; wherein $R^1$ is defined above.

Examples of preferred ruthenium complexes having monodentate ligands are shown below.

[Ru(Im)$_6$]Cl$_2$ where Im=imidazole
[Ru (1-MeIm)$_6$]Cl$_2$ where 1-MeIm=1-methyl imidazole
[Ru(1-MeIm)$_6$](PF$_6$)$_3$
[Ru(1-MeIm)$_6$]Cl$_3$
[Ru(Im)$_6$]Cl$_3$ General procedures for making ruthenium complexes having six monodentate ligands are described in the exemplification section.

In another embodiment, a ruthenium complex can be made having multidentate ligands, in combination with other multidentate ligands and/or monodentate ligands. Suitable heterocyclic aromatic amine bidentate ligands will include, but are not limited to, imidazole based ligands (e.g., 2,2'-bis-(1-methylimidazolyl)phenylhydroxymethane); pyrazole based ligands (e.g., potassium-bis-pyrazolyl borate, bispyrazolyl methane); quinoline based ligands (e.g., 2,2'-bis(quinolinyl)phenylmethoxymethane); and quinazoline based ligands (2,2'-bis-(quinazolinyl)phenylmethoxymethane). Preferred are imidazole based ligands having the general formula:

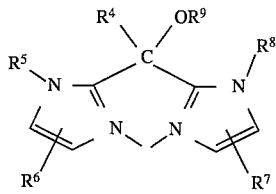

where each $R^4$ to $R^9$ may be the same or different and are independently selected from the substituents defined above for $R^2$ and $R^3$.

Examples of tridentate aromatic heterocyclic amine ligands include imidazole based ligands (e.g., bis-(2,-imidazolylmethyl)amine); pyrazole based ligands (e.g., potassium tris pyrazolyl borate); quinoline based ligands (e.g., 2,2'-bis-(quinolinylmethyl)amine, tris-(quinolinyl)methane).

It has now been discovered that the ruthenium complexes of this invention possess immunosuppressive activity as confirmed through a drug screen. Specific T cell proliferation was measured in response to antigen exposure in the presence or absence of ruthenium complexes. It was found that ruthenium complexes inhibited T cell proliferation by 50% (IC$_{50}$) at a concentration of about 10 to 100 nM. This compares favorably with cyclosporin A, which has an IC$_{50}$ at 15 nM. In an in vitro toxicity study, ruthenium complexes were found to be nontoxic to a Jurkat cell line when tested at the same concentrations that markedly inhibit T cell activation (Table 1). Additional ruthenium complexes that have immunosuppressive capability are described in U.S. patent application entitled "Methods for Inhibiting Immune Response" U.S. Ser. No. 08/331,204, filed Oct. 28, 1994, the entire teachings of which are incorporated herein by reference.

Ruthenium complexes can be administered orally, parenterally (e.g. intramuscularly, intravenously, subcutaneously), topically, nasally or via slow releasing microcarriers in dosage formulations containing a physiologically acceptable vehicle and optional adjuvants and preservatives. Suitable physiologically acceptable vehicles include saline, sterile water, creams, ointments or solutions.

Ruthenium complexes can be applied topically as a cream or ointment to locally deliver immunosuppressive concentrations of the drug without significant systemic exposure. Topical application may be the ideal way to deliver the compound in psoriasis and perhaps other inflammatory skin diseases such as contact dermatitis and pemphigus vulgaris.

The specific dosage level of active ingredient will depend upon a number of factors, including biological activity of the ruthenium complexes, age, body weight, sex, general health, severity of the particular disease to be treated and the degree of immune suppression desired, as well as appropriate pharmacokinetic properties. It should be understood that ruthenium complexes can be administered to mammals other than humans for immunosuppression of mammalian autoimmune diseases.

Ruthenium complexes can be administered in combination with other drugs to boost the immunosuppressive effect. Compounds that can be coadministered include steroids (e.g. methyl prednisolone acetate), NSAIDS and other known immunosuppressants such as azathioprine, 15-deoxyspergualin, cyclosporin, mizoribine, mycophenolate mofetil, brequinar sodium, leflunomide, FK-506, rapamycin and related molecules. Dosages of these drugs will also vary depending upon the condition and individual to be treated.

The assay used to measure T cell growth inhibition was a human peripheral blood lymphocyte (PBL) proliferation assay using standard procedures known in the art. PBL's were chosen due to their known ability to proliferate in the presence of antigens derived from herpes simplex virus (HSV), Rubella or tetanus toxoid (TT). PBL growth inhibition was measured in terms of ruthenium complexes's ability to interfere with antigen induced lymphocyte proliferation.

Ruthenium complexes can be used to produce antibodies (e.g., polyclonal and monoclonal) against the complexes. Methods for making antibodies are well known. The antibodies can be used as a diagnostic tool for monitoring the amount of ruthenium complex in patient blood levels. The ability to closely monitor the amount of ruthenium complex provides a suitable means for controlling drug delivery to patients in both preclinical and clinical settings.

The invention will be further illustrated by the following non-limiting Examples:

EXAMPLE 1—Preparation of [Ru(1-MeIm)$_6$]Cl$_2$

RuCl$_3$ (1.871 g, 9.04 mmol) was added slowly to 1-MeIm (10 mL, 125 mmol, 14 eq.). The mixture was placed in a preheated oil bath (230° C.), and the mixture was refluxed for 2 hours. The mixture was cooled down to room temperature and acetone (50–70 mL) was added to the mixture. The mixture was filtered and the solid washed with acetone (3×10 mL). The product was dried under vacuum.

The product was dissolved in MeOH (30 mL), and filtered over celite. The product was obtained as a light yellow crystalline (3.27 g, 55%) solid after triple crystallization from MeOH/ether.

[Ru(1-MeIm)$_6$]Cl$_2$ was characterized by X-ray crystallography, 1H NMR, UV/Vis and elemental analysis.

EXAMPLE 2—Preparation of [Ru(1-MeIm)$_6$]Cl$_3$

[Ru(1-MeIm)$_6$]Cl$_2$ (0.405 g, 0.609 mmol) was dissolved in HCl (0.25M, 30 mL) and H$_2$O$_2$ was added slowly until the starting material had disappeared (reaction followed by UV/Vis spectroscopy). The solvent was removed to dryness and the product was purified by recrystallization from MeOH/ether. The product was characterized by UV/Vis.

EXAMPLE 3—PBL Antigen Specific Proliferation Assay

The lymphocytes were prepared by first separating them from the blood samples of several donors by Ficoll gradient separation as described by standard procedure known in the art. The isolated lymphocytes were then grown in RPMI 1640 medium containing 5% human AB serum, glutamine (2 mM), penicillin/streptomycin, 50 µ/ml/50 µg/ml sodium pyruvate (1 mM) and HEPES buffer (10 mM).

For assay purposes, PBL's were incubated at a density of $10^5$ per 200 µl of medium per well of a 96-well plate.

Tetanus toxoid (TT; Connaught Labs, Willow Dale, ON) was used as a stimulating antigen at a concentration of 5 LF/ml.

The test wells containing PBL's, were exposed to tetanus toxoid antigen, along with various dilutions of the ruthenium complexes solutions, as shown in Table 1.

Subsequently, TT antigen/ruthenium complexes exposed PBL's were pulsed with 1 µCi/well of $^3$H-thymidine on day 5 using a standard procedure known in the art. The cells were then harvested 16 hours later onto a glass fiber filter using a TOMTEC cell harvester. Thymidine incorporation was measured by liquid scintillation counting using a Beta plate counter (Pharmacia, Inc., Piscataway, N.J.).

The results of the assay are shown in Table 1.

TABLE 1

| Structure | IC$_{50}$ (µg/mL) | Cytotoxicity (Jurkat cell) IC$_{50}$ (µg/mL) |
|---|---|---|
| [Ru(1-MeIm)$_6$]Cl$_2$ | 0.052 ± 0.03 | 2000 |
| [Ru(1-MeIm)$_6$](PF$_6$)$_3$ | 0.19 ± 0.16 | 115 |
| [Ru(1-MeIm)$_6$]Cl$_3$ | 0.12 ± 0.1 | >300 |
| [Ru(Im)$_6$]Cl$_2$ | 0.0067 ± 0.003 | 200 |
| [Ru(4-MeIm)$_6$]Cl$_2$ | 0.09 ± 0.07 | 1040[a] |
| [Ru(Im)$_6$]Cl$_3$ | 0.005 ± 0.004 | 530[a] | a. values are extrapolated

EQUIVALENTS

Those skilled in the art will recognize, or be able to ascertain, using no more than routine experimentation many equivalents to the specific embodiments of the invention described herein. Such equivalents are intended to be encompassed by the following claims:

We claim:

1. A ruthenium complex of the general formula:

[RuM$_m$]Z$_n$ wherein Ru is ruthenium having an oxidation state of 2 or 3;
    wherein M is the same or different and is independently a 5-membered ring that is a heterocyclic amine,
    wherein m is 6;
    wherein Z is a counterion of appropriate charge to render the overall charge of the complex neutral;
    wherein n is 0, 1, 2, 3 or 4.

2. The ruthenium complex of claim 1 wherein M is a heterocyclic aromatic amine selected from the group consisting of imidazole, triazole, pyrazole and their derivatives obtained by substituting for one or more hydrogen atoms with one or more of the following moieties C1–C5 alkyl, C2–C5 alkenyl, hydroxy, nitro, amino, carboxyl, ester, di-C1–C4 alkyl amine, phenyl, benzyl and combinations thereof.

3. The ruthenium complex of claim 2 wherein the imidazole has the general formula:

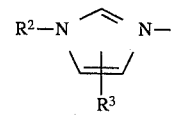

where R$^2$ and R$^3$ are independently selected from the group consisting of aryl, heteroaryl, linear and branched alkyl, —C(O)H, —COOR$^1$, —CONR$^1$, —COOH, methyl, H, Cl, Br, I and NO$_2$; wherein R$^1$ is a linear or branched alkyl or aryl.

4. The ruthenium complex of claim 3 wherein the ruthenium complex is selected from the group consisting of:
    a) [Ru(Im)$_6$]Cl$_2$ where Im=imidazole;
    b) [Ru(1-MeIm)$_6$]Cl$_2$ where 1-MeIm=1-methyl imidazole;
    c) [Ru(1-MeIm)$_6$](PF$_6$)$_3$;
    d) [Ru(1-MeIm)$_6$]Cl$_3$;
    e) [Ru(Im)$_6$]Cl$_3$; and
    f) [Ru(4-MeIm)$_6$]Cl$_2$.

5. The ruthenium complex of claim 1 wherein Z is a counterion selected from the group consisting of F$^-$, Cl$^-$, Br$^-$, I$^-$, NO$_3^-$, NH$_4^+$, NR$_4^{1+}$, PF$_6^-$, SO$_4^{-2}$, R$^1$ImH$^+$, BPh$_4^-$ and ClO$_4^-$; wherein Im is imidazole and R$^1$ is a linear or branched alkyl or aryl.

* * * * *

UNITED STATES PATENT AND TRADEMARK OFFICE
CERTIFICATE OF CORRECTION

PATENT NO. : 5,512,687
DATED : April 30, 1996
INVENTOR(S) : Cecilia M. Bastos

It is certified that error appears in the above-indentified patent and that said Letters Patent is hereby corrected as shown below:

In Claim 1, Column 6, line 11, after "heterocyclic" insert --aromatic--.

Signed and Sealed this

Eighth Day of October, 1996

Attest:

BRUCE LEHMAN

Attesting Officer

Commissioner of Patents and Trademarks